(12) United States Patent
Colborn et al.

(10) Patent No.: US 7,818,069 B2
(45) Date of Patent: Oct. 19, 2010

(54) RIBBON ELECTRODE

(75) Inventors: John C. Colborn, League City, TX (US); J. Nick Marsh-Chetter, Houston, TX (US); Shawn D. Kollatschny, Pearland, TX (US); Bryan Byerman, League City, TX (US)

(73) Assignee: Cyberonics, Inc., Houston, TX (US)

( * ) Notice: Subject to any disclaimer, the term of this patent is extended or adjusted under 35 U.S.C. 154(b) by 210 days.

(21) Appl. No.: 11/829,372

(22) Filed: Jul. 27, 2007

(65) Prior Publication Data

US 2009/0030493 A1 Jan. 29, 2009

(51) Int. Cl.
*A61N 1/00* (2006.01)

(52) U.S. Cl. ........................................ 607/116; 607/152

(58) Field of Classification Search .................. 607/115, 607/116, 117, 118, 124, 126, 130, 149, 152
See application file for complete search history.

(56) References Cited

U.S. PATENT DOCUMENTS

| | | | |
|---|---|---|---|
| 274,262 A * | 3/1883 | Heilman et al. ............. | 400/164 |
| 3,421,511 A | 1/1969 | Terry, Jr. | |
| 3,760,812 A | 9/1973 | Timm et al. | |
| 3,796,211 A | 3/1974 | Kohl | |
| 4,305,402 A | 12/1981 | Katims | |
| 4,384,926 A | 5/1983 | Wagner | |
| 4,458,696 A * | 7/1984 | Larimore .................... | 607/152 |
| 4,459,989 A | 7/1984 | Borkan | |
| 4,508,053 A | 4/1985 | Eriksson | |
| 4,573,481 A | 3/1986 | Bullara ....................... | 128/784 |
| 4,590,946 A | 5/1986 | Loeb | |
| 4,608,985 A | 9/1986 | Crish et al. | |
| 4,612,934 A | 9/1986 | Borkan | |
| 4,628,942 A | 12/1986 | Sweeney et al. | |
| 4,649,936 A | 3/1987 | Ungar et al. | |
| 4,702,254 A | 10/1987 | Zabara ........................ | 128/421 |
| 4,793,353 A | 12/1988 | Borkan | |
| 4,827,932 A * | 5/1989 | Ideker et al. .................... | 607/2 |
| 4,850,356 A | 7/1989 | Heath | |
| 4,860,616 A | 8/1989 | Smith | |
| 4,867,164 A | 9/1989 | Zabara ........................ | 128/421 |
| 4,920,979 A | 5/1990 | Bullara | |

(Continued)

FOREIGN PATENT DOCUMENTS

EP 1145736 A2 10/2001

*Primary Examiner*—Mark W Bockelman
*Assistant Examiner*—Elizabeth K So
(74) *Attorney, Agent, or Firm*—Conley Rose, P.C.; Timothy L. Scott

(57) ABSTRACT

We disclose an electrode assembly comprising a ribbon electrode having a first surface and a second surface; a plurality of bosses disposed on the second surface of the ribbon electrode, wherein each boss has a third surface substantially not in contact with the second surface of the ribbon electrode and at least one boss is electrically conducting; and an insulator contacting substantially the entire second surface of the ribbon electrode and substantially the entire third surface of each boss; wherein the insulator is substantially not in contact with the first surface of the ribbon electrode. We also disclose an implantable medical device system comprising an implantable medical device for generating an electrical signal; an electrode assembly as described; and a lead wire electrically coupled to both the implantable medical device and at least one electrically conducting boss of the electrode assembly.

17 Claims, 8 Drawing Sheets

U.S. PATENT DOCUMENTS

| | | | |
|---|---|---|---|
| 4,979,511 A | 12/1990 | Terry, Jr. | 128/642 |
| 5,003,975 A | 4/1991 | Hafelfinger et al. | |
| 5,025,807 A | 6/1991 | Zabara | 128/421 |
| 5,095,905 A | 3/1992 | Klepinski | |
| 5,146,920 A | 9/1992 | Yuuchi et al. | |
| 5,154,172 A | 10/1992 | Terry, Jr. et al. | 128/419 R |
| 5,188,104 A | 2/1993 | Wernicke et al. | 128/419 R |
| 5,215,086 A | 6/1993 | Terry, Jr. et al. | 128/421 |
| 5,215,089 A | 6/1993 | Baker, Jr. | |
| 5,231,988 A | 8/1993 | Wernicke et al. | 128/421 |
| 5,251,634 A | 10/1993 | Weinberg | |
| 5,263,480 A | 11/1993 | Wernicke et al. | 607/118 |
| 5,269,303 A | 12/1993 | Wernicke et al. | 607/45 |
| 5,299,569 A | 4/1994 | Wernicke et al. | 607/45 |
| 5,304,206 A | 4/1994 | Baker, Jr. et al. | 607/2 |
| 5,330,515 A | 7/1994 | Rutecki et al. | 607/46 |
| 5,335,657 A | 8/1994 | Terry, Jr. et al. | 607/45 |
| 5,351,394 A | 10/1994 | Weinberg | |
| 5,531,778 A | 7/1996 | Maschino et al. | 607/118 |
| 5,571,150 A | 11/1996 | Wernicke et al. | 607/72 |
| 5,575,813 A | 11/1996 | Edell et al. | |
| 5,707,400 A | 1/1998 | Terry, Jr. et al. | 607/44 |
| 5,916,239 A | 6/1999 | Geddes et al. | 607/14 |
| 6,052,624 A | 4/2000 | Mann | |
| 6,259,951 B1 | 7/2001 | Kuzma et al. | |
| 6,304,787 B1 | 10/2001 | Kuzma et al. | |
| 6,393,325 B1 | 5/2002 | Mann et al. | |
| 6,418,348 B1 | 7/2002 | Witte | |
| 6,473,653 B1 | 10/2002 | Schallhorn et al. | |
| 6,477,417 B1 | 11/2002 | Levine | |
| 6,510,332 B1 | 1/2003 | Greenstein | |
| 6,587,719 B1 | 7/2003 | Barrett et al. | 607/2 |
| 6,600,956 B2 | 7/2003 | Maschino et al. | |
| 6,600,957 B2 * | 7/2003 | Gadsby | 607/142 |
| 6,606,523 B1 | 8/2003 | Jenkins | |
| 6,609,025 B2 | 8/2003 | Barrett et al. | 607/2 |
| 6,622,041 B2 | 9/2003 | Terry, Jr. et al. | 607/9 |
| 6,907,295 B2 | 6/2005 | Gross et al. | |
| 7,467,016 B2 | 12/2008 | Colborn | |
| 2003/0144711 A1 | 7/2003 | Pless et al. | |
| 2003/0195601 A1 * | 10/2003 | Hung et al. | 607/116 |
| 2003/0236558 A1 | 12/2003 | Whitehurst et al. | |
| 2004/0015205 A1 | 1/2004 | Whitehurst et al. | |
| 2004/0167583 A1 | 8/2004 | Knudson et al. | |
| 2004/0172088 A1 | 9/2004 | Knudson et al. | |
| 2004/0172094 A1 | 9/2004 | Cohen et al. | |
| 2005/0016657 A1 | 1/2005 | Bluger | |
| 2005/0038484 A1 | 2/2005 | Knudson et al. | |
| 2005/0131485 A1 | 6/2005 | Knudson et al. | |
| 2006/0058597 A1 | 3/2006 | Machado et al. | |
| 2007/0173914 A1 | 7/2007 | Kollatschny | |

* cited by examiner

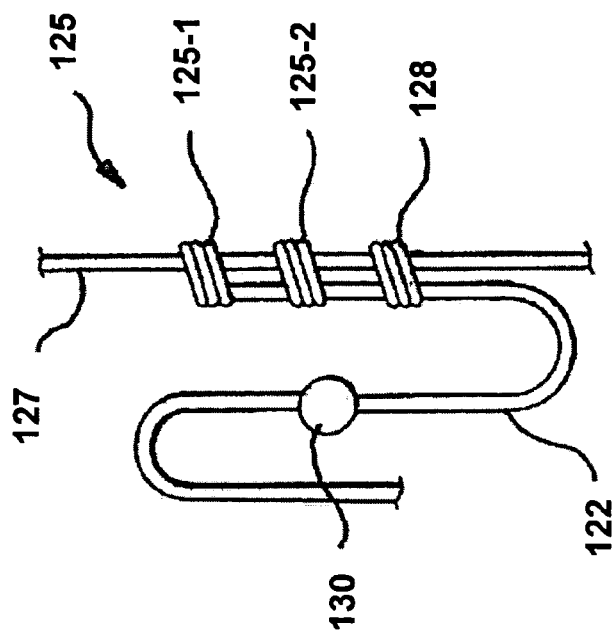
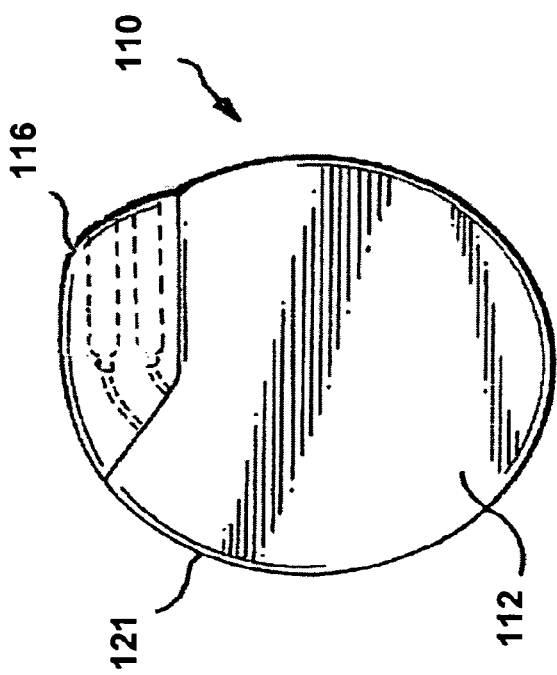
FIGURE 1B
FIGURE 1C

RIBBON ELECTRODE

BACKGROUND OF THE INVENTION

1. Field of the Invention

This invention relates generally to medical devices and, more particularly, to methods, apparatus, and systems using an improved electrode for providing electrical signal therapy to a target body tissue of a patient.

2. Description of the Related Art

A variety of electrical or neural activity constantly occurs throughout the human body. For example, the central nervous system (CNS) is generally a hub of electrical or neural activity requiring appropriate coordination. The brain supervises the central nervous system (CNS). Properly controlled electrical or neural activity enables the brain to coordinate various mental and body functions to maintain homeostasis.

In addition to a drug regimen or surgical intervention, potential treatments for many diseases and disorders include implantation of a medical device in a patient for providing electrical signal therapy to body tissue, which may be referred to as "electrical stimulation." In particular, by selectively applying therapeutic electrical signals to one or more electrodes coupled to the patient's neural tissue, an implantable medical device (IMD) may electrically stimulate a target tissue location. This device may be used to sense or treat a patient's physiologic parameter, disease, condition or disorder. (The word "or" is used herein in the inclusive sense, i.e., "and/or" or "A, B, or both," unless a particular instance of it is expressly indicated to be in the exclusive sense).

Therapeutic electrical signals have been used to apply an electrical signal to a variety of neural structures of the body, including, more particularly, cranial nerves such as the vagus nerve. To provide vagus nerve stimulation to a patient, a neurostimulator device may be implanted in a target location in the patient's body. Such a neurostimulator device system may comprise an electrical signal generator, attached to an electrical lead having one or more electrodes coupled to the vagus nerve. For example, a method of providing electrical neurostimulation therapy to a patient may comprise applying a stimulus to an electrode coupled to a branch or a main trunk of a selected cranial nerve of the patient.

The signal may be used to induce afferent action potentials on the nerve and thereby increase the flow of neural signals up the nerve, toward the brain. The signal may also (or alternatively) generate efferent action potentials to modulate a neural response in one or more body structures of the patient, such as any of the numerous organs innervated by efferent signals on the vagus nerve. Finally, therapeutic electrical signals may also or additionally be used to inhibit neural activity or to block neural impulses from moving up or down the nerve the nerve. As used herein, the terms "stimulate" and "modulate" are interchangeable and refer to delivery of a signal (which may comprise an electrical, magnetic, or chemical stimulus) to a target body area, regardless of whether its effects include generation of afferent action potentials, generation of efferent action potentials, or the blocking of endogenous action potentials. Therapeutic electrical stimulation of the vagus nerve has been used to treat epilepsy and depression.

More generally, the endogenous electrical activity (i.e., activity attributable to the natural functioning of the patient's own body) of a neural structure of a patient may be modulated in a variety of ways. In particular, the electrical activity may be modulated by exogenously applied (i.e., from a source other than the patient's own body) electrical, chemical, or mechanical signals applied to the neural structure. The modulation (hereinafter referred to generally as "neurostimulation" or "neuromodulation") may involve the induction of afferent action potentials, efferent action potentials, or both, in the neural structure, and may also involve blocking or interrupting the transmission of endogenous electrical activity traveling along the nerve. Electrical neurostimulation or modulation of a neural structure refers to the application of an exogenous electrical signal (as opposed to a magnetic, chemical or mechanical signal), to the neural structure. Electrical neurostimulation may be provided by implanting an electrical device underneath the skin of a patient and delivering an electrical signal to a nerve such as a cranial nerve. The electrical neurostimulation may involve performing a detection, with the electrical signal being delivered in response to a detected physiologic parameter. This type of stimulation is generally referred to as "active," "feedback," "closed loop," or "triggered" stimulation. Alternatively, the system may operate without a detection system once the patient has been diagnosed with epilepsy (or another medical condition), and may periodically apply a series of electrical pulses to the nerve (e.g., a cranial nerve such as a vagus nerve) intermittently throughout the day, or over another predetermined time interval. This type of stimulation is generally referred to as "passive," "non-feedback," "open loop," or "prophylactic," stimulation. The stimulation may be applied by an implantable medical device that is implanted within the patient's body.

Many types of electrodes have been developed to facilitate electrical signal therapy for a target neural structure. For example, circumneural electrodes surround a portion of a nerve longitudinally to provide electrical stimulation of the nerve. The electrical stimulation may modulate electrical signals or impulses carried by the nerve. Alternatively or additionally, an electrode may sense electrical signals carried by the nerve. For example, a medical device, such as an implantable medical device may use such an electrode to stimulate or sense nerve activity on a portion of a tissue.

SUMMARY OF THE INVENTION

In one aspect, the present invention comprises an implantable medical device system for treating a patient with a medical condition. The implantable medical device system comprises (i) an implantable medical device for generating an electrical signal; (ii) an electrode assembly comprising a ribbon electrode having a first surface and a second surface; a plurality of bosses disposed on the second surface of the ribbon electrode, wherein each boss has a third surface substantially not in contact with the second surface of the ribbon electrode and at least one boss is electrically conducting; and an insulator contacting substantially the entire second surface of the ribbon electrode and substantially the entire third surface of each boss; wherein the insulator is substantially not in contact with the first surface of the ribbon electrode; and (iii) a lead wire electrically coupled to both the implantable medical device and at least one electrically conducting boss.

In a further aspect, an electrode assembly for delivering an electrical signal to a portion of a first tissue of a patient's body is provided. The electrode assembly comprises a ribbon electrode having a first surface and a second surface; a plurality of bosses disposed on the second surface of the ribbon electrode, wherein each boss has a third surface substantially not in contact with the second surface of the ribbon electrode and at least one boss is electrically conducting; and an insulator contacting substantially the entire second surface of the ribbon electrode and substantially the entire third surface of each boss; wherein the insulator is substantially not in contact with the first surface of the ribbon electrode.

In another aspect, an electrode assembly is provided, comprising an electrode formed in a substantially flat, cylindrical, spiral, or helical conformation having a first surface and a second surface; a plurality of formations disposed on the second surface of the electrode, wherein each formation has a third surface substantially not in contact with the second surface of the electrode and at least one formation is electrically conducting; and an insulating material contacting substantially the entire second surface of the electrode and substantially the entire third surface of each formation; wherein the insulating material is substantially not in contact with the first surface of the electrode.

BRIEF DESCRIPTION OF THE DRAWINGS

The invention may be understood by reference to the following description taken in conjunction with the accompanying drawings, in which like reference numerals identify like elements, and in which:

FIGS. 1A-1C are stylized diagrams of an implantable medical device implanted into a patient's body for providing electrical stimulation to a portion of the patient's body, in accordance with one illustrative embodiment of the present invention;

Figure 1A:
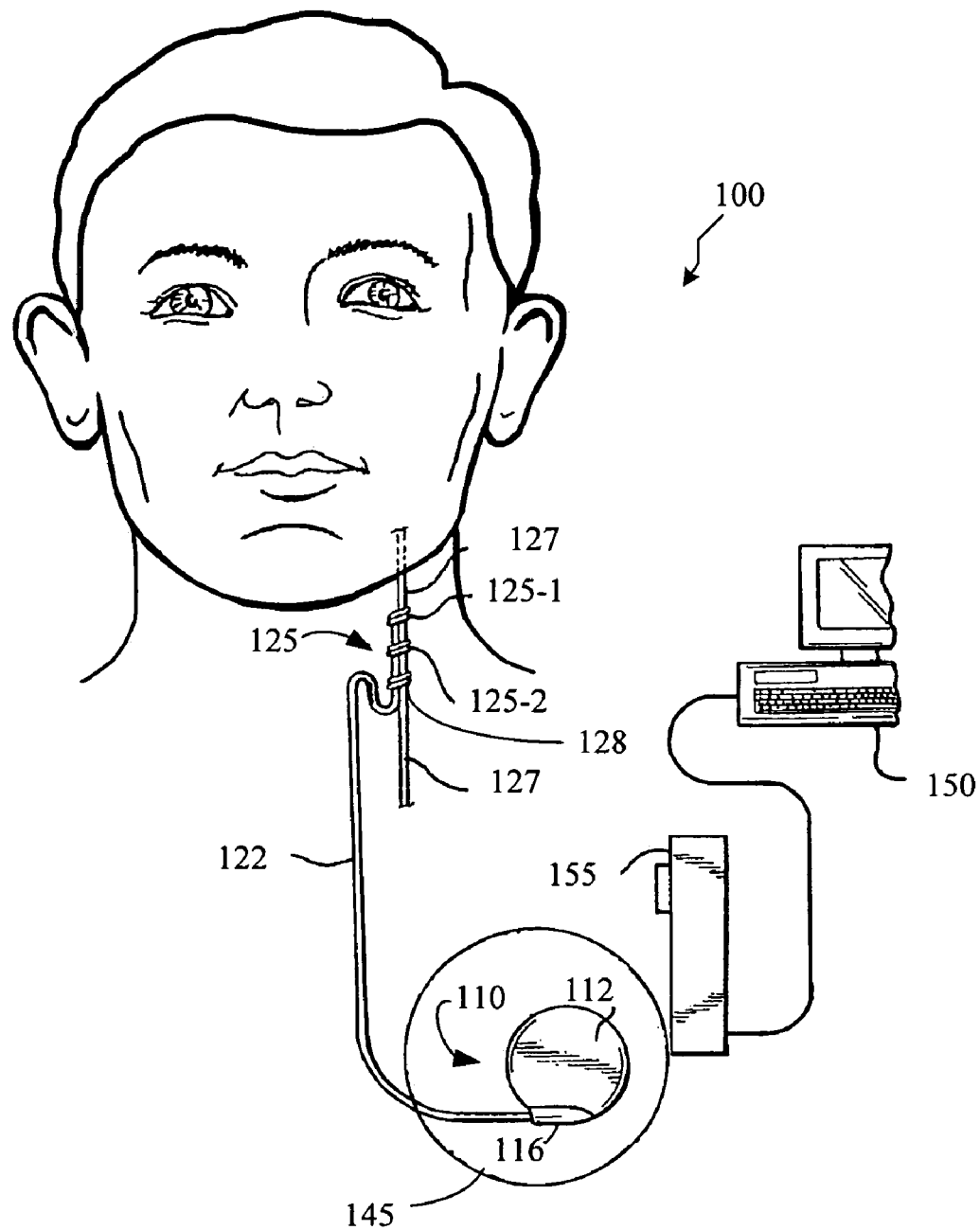

While the invention is susceptible of various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), or electrodes that are capable of delivering a stimulation signal, as well as performing a sensing function.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pats. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult. Moreover, even if such pathways were known, the precise stimulation parameters that would modulate particular pathways relevant to a particular disorder generally cannot be predicted.

Generally, embodiments of the present invention relate to electrodes, and more particularly to an insulated electrode, such as a circumferential neural (circumneural) electrode for implantation on a selected nerve tissue of a patient. The insulated electrode may be adapted to selectively provide electrical stimulation or detect a signal on a nerve. Some embodiments of the present invention use the insulated electrode for applying an electrical signal from an implantable medical device (IMD) to a nerve of a patient. The electrical signal may exogenenously generate action potentials on the nerve or detect native (i.e., endogenous) action potentials on the nerve. In one embodiment, a neurostimulation signal on the insulated electrode may provide a desired therapeutic effect substantially without affecting unintended portions of the nerve fibers or generating additional unintentional (exogenously induced) electrical activity on the nerve, or both.

The implantable medical device may be an implantable medical device that is capable of providing an electrical signal to the insulated electrode for modulating the electrical activity on the nerve to provide a therapeutic effect. Some embodiments of the present invention provide for methods, apparatus, and systems to selectively provide an electrical signal to a nerve of a patient using a multi-channel electrode. Other embodiments of the present invention provide for methods, apparatus, and systems to selectively detect an electrical signal from a nerve of a patient using a multi-channel electrode. In certain embodiments, the nerve comprises a cranial nerve, such as a vagus nerve. In this way, the insulated electrode may selectively provide stimulation to a nerve, such as the vagus nerve (cranial nerve X), from an implantable medical device (IMD), such as a neurostimulator, to treat a disorder or a medical condition, e.g., a neuropsychiatric disorder such as depression, an epilepsy disorder, a gastric-related disorder, a hormonal disorder, a reproductive disorder, a metabolic disorder, a hearing disorder, a pain disorder, or a heart rhythm disorder, among others.

An implantable medical device system for treating a patient with a medical condition may comprise an implantable medical device (IMD) for generating an electrical signal. The IMD system further comprises an electrode operatively coupled to the IMD for delivering the electrical signal to a target portion of a tissue. The electrode comprises a first surface of which at least a portion directly couples to (i.e., directly contacts) the target portion of the first tissue, a second surface that does not contact the target portion of the first tissue, and an insulator disposed on the electrode to form an insulating barrier between at least a portion of the second surface and at least a portion of a body tissue other than the target portion of the first tissue.

An IMD system may collect data to diagnose a patient's medical condition. Embodiments of the present invention provide for an insulated electrode capable of use with a neurostimulator system for treatment of disorders, e.g., depression disorder, an epilepsy disorder, a gastric-related disorder, a hormonal disorder, a reproductive disorder, a metabolic disorder, a hearing disorder, a pain disorder, or a heart rhythm disorder, among others.

The IMD may comprise a controller to selectively provide an electrical stimulation signal to the electrode, or to detect an endogenous electrical signal using the electrode. The term "controller" may include one or more of a variety of control mechanisms, such as a hardware controller, a software controller, a firmware controller, or a combination or two or more thereof. The term "electrode" may refer to a single electrode, or may refer to a plurality of insulated electrodes, each insulated electrode corresponding to stimulation or sensing channel. The controller may be capable of selecting one or more channels for the plurality of insulated electrodes.

Persons of skill in the art will appreciate that many electrode designs could be used in the present invention. Structurally, an electrode assembly may comprise at least one, e.g., two, insulated electrodes comprising a conductive material such as platinum, iridium, platinum-iridium alloys, or oxides of the foregoing. The term "ribbon electrode" as used herein refers to any electrode that is substantially thin, that is, has one spatial dimension that is no more than one-tenth the length of the other two spatial dimensions. The ribbon electrode can be substantially flat over its entire length, or it can form a cylinder, spiral, or helix. The electrode may sense or detect any target parameter in the patient's body. For example, the electrode coupled to the patient's vagus nerve may detect an intrinsic neural signal. The electrode may sense or detect an electrical signal (e.g., a voltage indicative of intrinsic neural electrical activity). The electrode, in some embodiments of the present invention, may administer an electrical stimulation therapy to the vagus nerve. Some embodiments of the present invention use a continuous, periodic or intermittent stimulation signal applied to the vagus nerve.

An exemplary IMD that may be implanted into a patient's body for providing a signal to a portion of the patient's body is described below according to one illustrative embodiment of the present invention. FIGS. 1A-1C depict a stylized implantable medical system 100 for implementing one or more embodiments of the present invention. FIGS. 1A-1C illustrate an electrical signal generator 110 having a main body 112 comprising a case or shell 121 (FIG. 1B) with a header 116 (FIG. 1B) for connecting to at least one lead 122. The electrical signal generator 110 is implanted in the patient's chest in a pocket or cavity formed by the implanting surgeon just below the skin (indicated by a line 145, FIG. 1A), similar to the implantation procedure for a pacemaker pulse generator.

A stimulating nerve electrode assembly 125 is conductively coupled to the distal end of an insulated, electrically conductive lead assembly 122, which preferably comprises one wire for each electrode of the electrode assembly 125. Lead assembly 122 is conductively coupled at its proximal end to the connectors on the header 116 on case 121. The electrode assembly 125 may be surgically coupled to a vagus nerve 127 in the patient's neck (FIG. 1A) or at another location, e.g., near the patient's diaphragm (not shown). The electrical neurostimulation signal may also be applied to other cranial nerves. The electrode assembly 125 is preferably wrapped around the vagus nerve, and the electrode assembly 125 may be secured to the nerve 127 by a spiral anchoring tether 128 (FIG. 1C) such as that disclosed in U.S. Pat. No. 4,979,511 issued Dec. 25, 1990 to Reese S. Terry, Jr. and assigned to the same assignee as the instant application. Lead assembly 122 can be secured, while retaining the ability to flex with movement of the chest and neck, by a suture connection 130 to nearby tissue (FIG. 1C).

In one embodiment, the electrode assembly 125 has an open helical design, which is self-sizing and flexible to minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises at least one ribbon electrode, of a conductive material such as platinum, iridium, platinum-iridium alloys, or oxides of the foregoing.

In one embodiment, the IMD is used to perform active stimulation in response to a stimulus received by the IMD from a sensor. Other embodiments of the present invention use passive stimulation to deliver a continuous, periodic, or intermittent electrical signal to the vagus nerve according to a programmed on/off duty cycle without the use of sensors to trigger therapy delivery. Both passive and active stimulation may be combined or delivered by a single IMD according to the present invention. Either or both modes may be appropriate to treat the particular disorder diagnosed in the case of a specific patient under observation.

The electrical signal generator 110 may be programmed with an external computer 150 using programming software of the type copyrighted by the assignee of the instant application with the Register of Copyrights, Library of Congress, or other suitable software based on the description herein. In one embodiment, a programming wand 155 can be used to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator. In an embodiment using RF frequencies in the Medical Implants Communiations Service (MICS) bands, the wand 155 may be omitted.

By providing the stimulation therapy, the electrical signal generator 110 may treat a disorder or a medical condition of a patient. A generally suitable form of neurostimulator for use in the method and apparatus of the present invention is disclosed, for example, in U.S. Pat. No. 5,154,172, assigned to the same assignee as the present application. A commercially available example of such a neurostimulator is the NeuroCybernetic Prosthesis (NCP®, Cyberonics, Inc., Houston, Tex., the assignee of the present application). Certain parameters of the electrical signal generated by the electrical signal generator 110 are programmable, such as by means of an external programmer in a manner conventional for implantable electrical medical devices.

Figure 2:
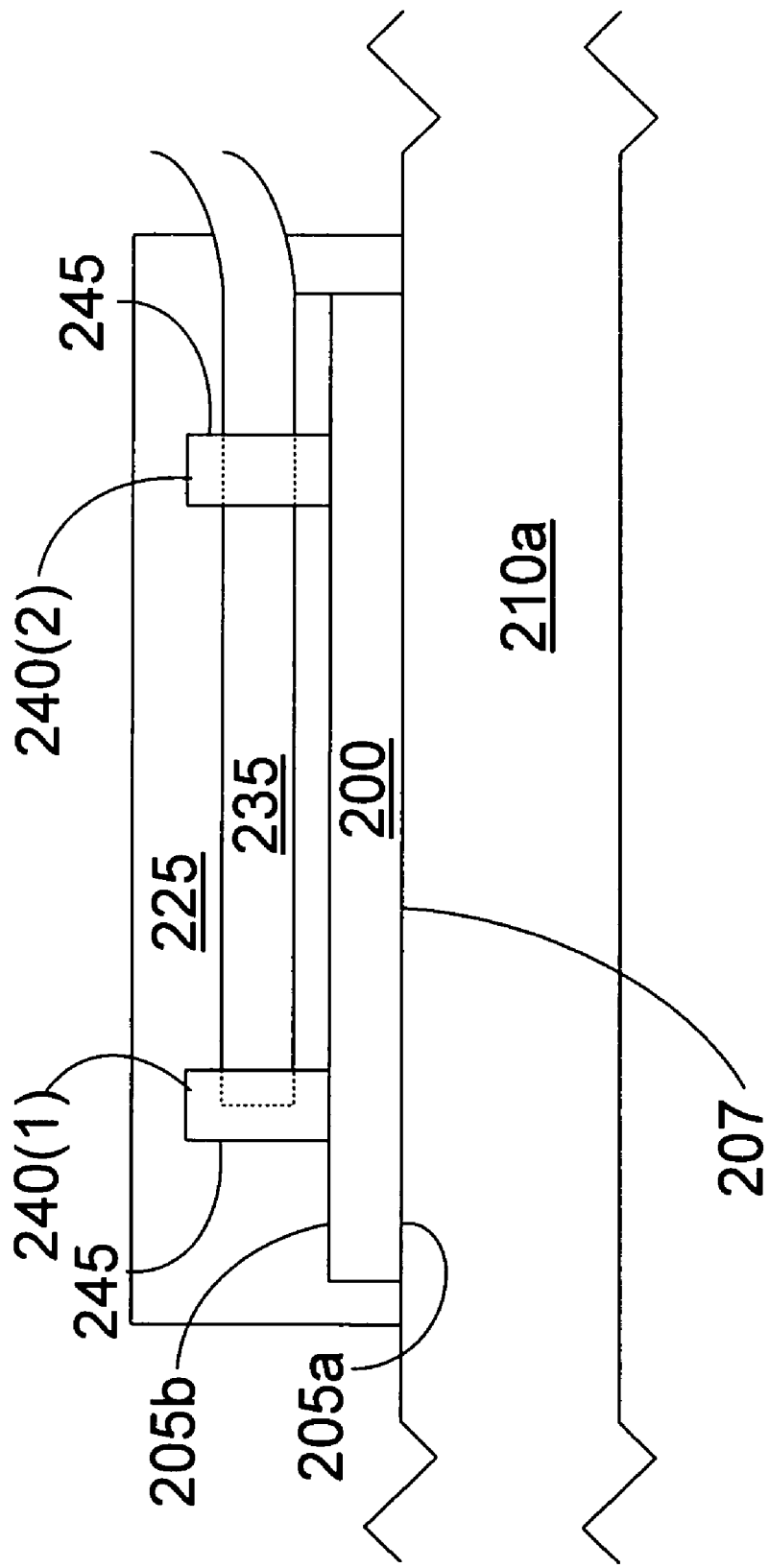
FIG. 2 is a cross sectional view of an electrode assembly, in accordance with one illustrative embodiment of the present invention.

Turning to FIG. 2, the electrode assembly 125 is shown in more detail. The electrode assembly 125 comprises a ribbon electrode 200 having a first surface 205a and a second surface 205b; a plurality of bosses 240(1), 240(2), etc. disposed on the second surface 205b of the ribbon electrode 200, wherein each boss (generally, 240) has a third surface 245 substantially not in contact with the second surface 205b of the ribbon electrode 200 and at least one boss 240 is electrically conducting; and an insulator 225 contacting at least part of the second surface 205b of the ribbon electrode 200 and at least part of the third surface 245 of at least one boss (generally, 240). In one embodiment, the insulator 225 is substantially not in contact with the first surface 205a of the ribbon electrode 200. In one embodiment, the insulator 225 contacts substantially the entire second surface 205b and substantially the entire third surface 245 of each boss (generally, 240).

The ribbon electrode 200 has a first surface 205a that couples to a first surface 207 of a first tissue 210a, and a second surface 205b, and it may provide stimulation to the first tissue 210a. In one embodiment, the first surface 205a may directly contact the first surface 207 of the first tissue. The ribbon electrode 200 may also sense an intrinsic or a native signal from the first tissue 210a. Consistent with one embodiment of the present invention, the ribbon electrode 200 may comprise at least two insulated electrodes 125-1, 125-2, such as a pair of cylindrical electrodes that may be spaced apart. Examples of the first tissue 210a include, e.g., a nerve 127 or an anatomical structure having a surface to which the first surface 205a can be conformed, such as an anatomical structure having a planar, cylindrical or generally round surface, e.g., a muscle or an organ (not shown).

The ribbon electrode 200 may be continuous, or it can have discontinuities across a portion of its width to allow flexion of the ribbon electrode.

The term "boss" is used herein to refer to any structure 240(1), 240(2), etc. (generally, 240) raised above the second surface 205b of the ribbon electrode 200. The boss 240 provides a molding surface to facilitate adhesion of the insulator 225 to the ribbon electrode 200. The shape or the material of the boss 240 is not crucial provided adhesion of the insulator 225 can be achieved. Exemplary bosses 240 can be arcuate structures, forming saddles or tunnels above the second surface 205b; or coiled wires, forming half-loops above the second surface 205b. Another exemplary boss 240 is a linear structure having a long axis substantially perpendicular to the long axis of the second surface 205b and having a length substantially the same as the width of the second surface 205b. Whatever the shape, the surface area of the boss 240 that is not in contact with or continuous with the second surface 205b of the ribbon electrode 200 forms the third surface 245. Also, the location of bosses 240(1), 240(2), etc. on the second surface 205b of the ribbon electrode 200 is not critical.

In one embodiment, the dimensions of the boss 240 can be smaller than the length and the width of the second surface 205b, or smaller than the length.

In one embodiment, a boss 240 is integrally formed with the ribbon electrode 200, such as by stamping from the ribbon electrode 200 or crimping of the ribbon electrode 200.

In one embodiment, a boss 240 is separately formed from the ribbon electrode 200 and is subsequently affixed to the second surface 205b of the ribbon electrode 200, such as by welding or crimping to the ribbon electrode 200. Welding can include spot welding, laser welding, or other welding techniques known in the art. Other embodiments of the boss 240 may be implemented and remain within the spirit and scope of the present invention.

Figure 3A:
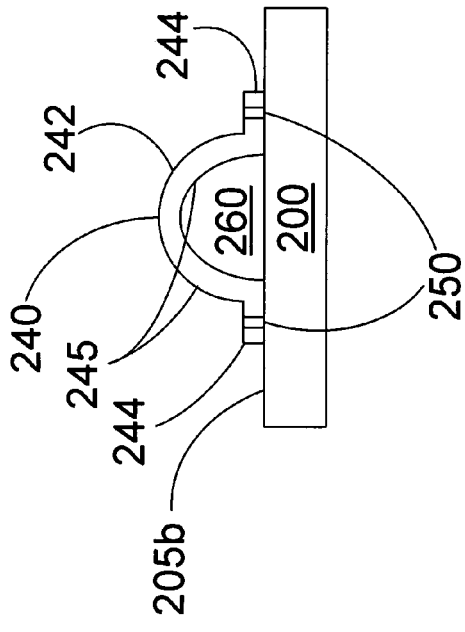
FIG. 3A is an overhead view of a partial electrode assembly, in accordance with one illustrative embodiment of the present invention.
Figure 3B:
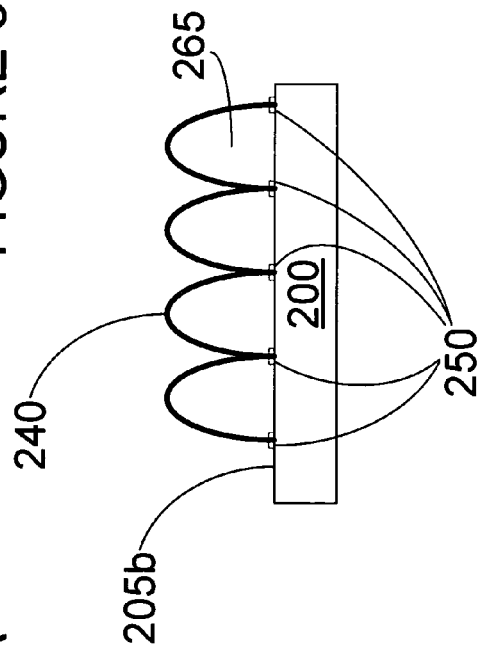
FIG. 3B is a cross sectional view of the partial electrode assembly shown in FIG. 3A, in accordance with one embodiment of the present invention.

FIGS. 3A and 3B depict stylized views of the ribbon electrode 200 and a boss 240 in accordance with illustrative embodiments of the invention. FIG. 3A shows an overhead view and FIG. 3B shows a cross sectional view, respectively. The boss 240 of this embodiment has an exemplary omega shape with an arcuate central portion 242 and a pair of affixment flanges 244 (FIG. 3B). The boss 240 of this embodiment is affixed to the second surface 205b of the ribbon electrode 200 by, for example, spot or laser welding between each affixment flange 244 and the ribbon electrode 200, forming welds 250. Other affixment techniques known in the art can be used. Affixment of the boss 240 to the second surface 205b of the ribbon electrode 200 defines a tunnel 260. The tunnel 260 can be used to physically couple, electrically couple, or both a lead 235 to the electrode assembly 125 (FIG. 2), to provide greater surface area 245 for attachment of insulator 225, or both. For example, insulator 225 may be molded to adhere to the second surface 205b and molding operation may encapsulate boss 240 using tunnel 260.

Figure 3C:
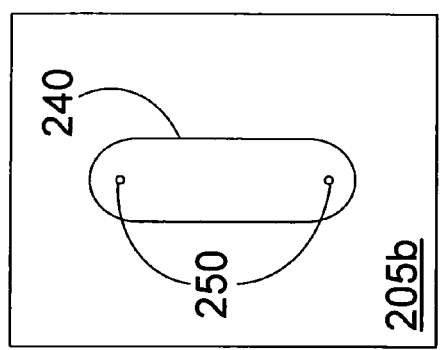
FIG. 3C is a cross sectional view of a partial electrode assembly, according to one illustrative embodiment of the present invention.

FIG. 3C shows a cross sectional view of another embodiment of a ribbon electrode 200 and a boss 240. The boss 240 of this embodiment may be a wire, such as a coiled wire, affixed by laser, spot, or sonic welds 250 to the second surface 205b of the ribbon electrode 200. Other affixment techniques known in the art can be used. Affixment of the boss 240 to the second surface 205b of the ribbon electrode 200 defines a aperture 265. The aperture 265 can be used to physically couple, electrically couple, or both a lead 235 to the electrode assembly 125, to provide greater surface area 245 for attachment of insulator 225, or both. For example, insulator 225 may encapsulate one or more bosses 240 to strongly adhere to the ribbon electrode 200.

The electrode assembly 125 may contain both integrally formed bosses 240 or separately formed bosses 240.

As stated above, at least one boss 240 is electrically conducting, by which is meant that electrical current applied to the third surface 245 of the boss 240 will be communicated with little resistance to the ribbon electrode 200.

The ribbon electrode 200 may be connected to a lead 235, which is welded to or otherwise secured to at least one boss 240, wherein at least one boss 240 is electrically conducting, in accordance with one embodiment of the present invention.

Any material that is not electrically conductive can be used as the insulator 225. In one embodiment, the insulator 225 is a silicone polymer.

In one embodiment of the electrode assembly 125, the insulator 225 contacts substantially the entire second surface 205b of the ribbon electrode 200 (excluding, as will be apparent to the skilled artisan, those portions of the second surface 205b to which bosses 240 may be affixed or formed from). In one embodiment, the insulator 225 contacts substantially the entire third surface 245 of each boss 240 (excluding, as will be apparent to the skilled artisan, those portions of the third surface 245 to which a lead 235 may be affixed). In one embodiment, the insulator 225 is substantially not in contact with the first surface 205a of the ribbon electrode 200. Any combination of the foregoing embodiments is possible, and preferably, all three embodiments are combined. In a preferred embodiment, the first surface 205a of the ribbon electrode 200 is free to form a substantially direct contact with the surface of a nerve tissue 210a. This is a distinguishing feature over known electrode designs, in which an insulator is typically wrapped over the edges of a first surface of an electrode, forming a relatively thick lip of insulator on a first surface and thereby creating a gap between a first surface of an electrode and a body tissue. As a result, the IMD may use a significantly less energy to obtain a desired stimulation threshold. This may promote an appreciable increase in the battery life of the IMD. Also, there would be less capacitance between the ribbon electrode 200 and the first surface 207 of the nerve tissue 210a, and therefore any body fluid between the ribbon electrode 200 and the nerve tissue 210a would be less likely to suffer from problems, such as protein degradation and potential slagging on the ribbon electrode 200, that may arise because of a net charge on the electrode attributable to the capacitance of the fluid. In addition, the ribbon electrode of the invention allows easier or better controlled manufacture relative to known designs.

In one embodiment, shown in FIG. 2, the electrode assembly 125 further comprises a lead wire 235 electrically coupled to at least one electrically conducting boss 240. The electrical coupling between the lead wire 235 and the at least one electrically conducting boss 240 allows current applied to the lead wire 235 (such as current generated by the IMD 100 or by an external medical device (not shown)) to flow into the electrically conducting boss 240 and thence into the ribbon electrode 200. One suitable method of coupling the lead wire(s) or cable 235 to the electrode assembly 125 comprises a spacer assembly such as that disclosed in U.S. Pat. No. 5,531,778, although other known coupling techniques may be used.

Although FIGS. 2-3 show the bosses 240(1), 240(2) as having long axes parallel to the long axis of the ribbon electrode 200, one or more bosses 240(1), 240(2) can be nonparallel to the long axis of the ribbon electrode 200. Nonparallelity may be suitable in designs in which the ribbon electrode 200 is helicated for wrapping around a nerve 127. In one embodiment, the long axis of each boss 240(1), 240(2), etc. is disposed at an angle, e.g., 6° off the long axis of the ribbon electrode 200. In one embodiment, bosses 240 may be placed with a variety of angles to the long or short axes of the ribbon electrode 200.

The electrode assembly 125 can have a plurality of generally spiral or helical structures that can partially or substantially completely wrap around a nerve 127. In one embodiment, a third loop 128 (which, in one embodiment, may have no electrode) acts as the anchoring tether 128 for the electrode assembly 125. In another embodiment, a loop containing an electrode acts as the anchoring tether 128 for the electrode assembly 125.

In operation, a plurality of ribbon electrodes 200 may deliver an electrical signal to the first surface 207 of the first tissue 210a. To this end, the lead 235 may use conducting elements to electrically couple a plurality of insulated electrodes 125-1, 125-2 to, e.g., a vagus nerve 127 as a cathode or a negative electrode and an anode or a positive electrode, respectively.

The ribbon electrode 200 may be implanted within the patient's body to provide electrical stimulation to a target tissue 210a. For example, the ribbon electrode 200 may neuromodulate the vagus nerve 127. Alternatively, or selectively, the ribbon electrode 200 may sense a neuropotential associated with the nerve 127. By implanting the ribbon electrode 200 within the patient's body, the insulated electrodes 125-1, 125-2 may stimulate the nerve 127.

In one embodiment, a therapy may be administered by stimulation of the patient's vagus nerve by an application of an electrical stimulation signal to the nerve 127. The ribbon electrode 200 may deliver an electrical signal to the selected cranial nerve manually or automatically. The ribbon electrode 200 may deliver the signal continuously, periodically or intermittently when activated.

For example, neurostimulation may be delivered as a pulsed electrical signal in discrete stimulation periods known as pulse bursts, which constitute a series of controlled electrical pulses defined by a plurality of parameters. The neurostimulation signal may be generated by an electrical pulse generator and applied to the vagus nerve 127 via the ribbon electrode 200. The parameters defining the neurostimulation signal may include a current magnitude, a pulse width, a pulse frequency, an on-time and an off-time.

However, in some embodiments, to provide vagus nerve stimulation (VNS) therapy, a patient's medical condition may also be monitored. Sensing-type electrodes, such as the ribbon electrodes 200 may be implanted at or near the vagus nerve. Using sensing electrodes(s), one or more body parameters relevant to the patient's medical condition may be detected and the sensed data may be compared to a reference value or range of reference values. If the sensed data relating to the patient's medical condition differs from the reference value or is outside the range of reference values over a given period, a therapeutic electrical neurostimulation signal may be applied. The therapeutic electrical neurostimulation signal may be applied periodically or applied as a result of patient intervention by manual activation using external control.

Figure 5:
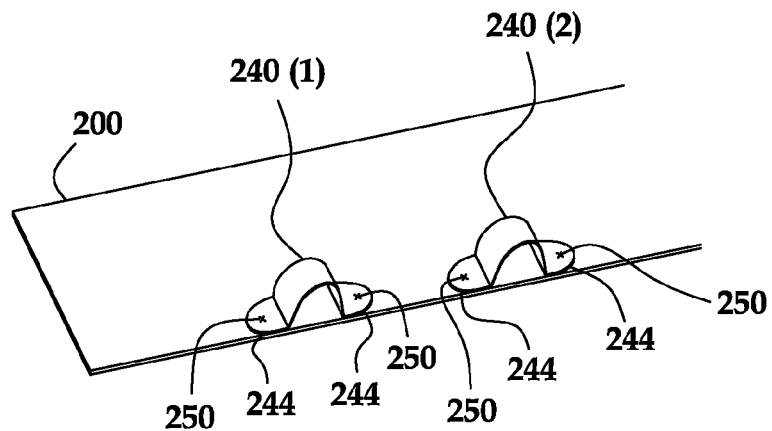
FIG. 5 is a perspective view of a partial electrode assembly having arcuate bosses affixed to the ribbon electrode by welding, according to one illustrative embodiment of the present invention.
Figure 6:
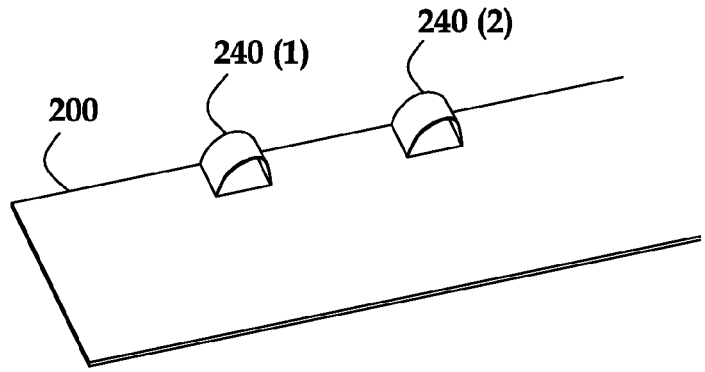
FIG. 6 is a perspective view of a partial electrode assembly having arcuate bosses stamped from the ribbon electrode, according to one illustrative embodiment of the present invention.

Elements of various embodiments of the electrode assembly 125 are shown in perspective in FIGS. 5-11. FIG. 5 is a perspective view similar to the embodiment shown in FIGS. 3A-3B and shows arcuate bosses 240(1), 240(2) affixed to the electrode by welds 250. FIG. 6 shows an embodiment somewhat like that of FIG. 5, but wherein the bosses 240(1), 240(2) are stamped from the ribbon electrode 200.

Figure 7:
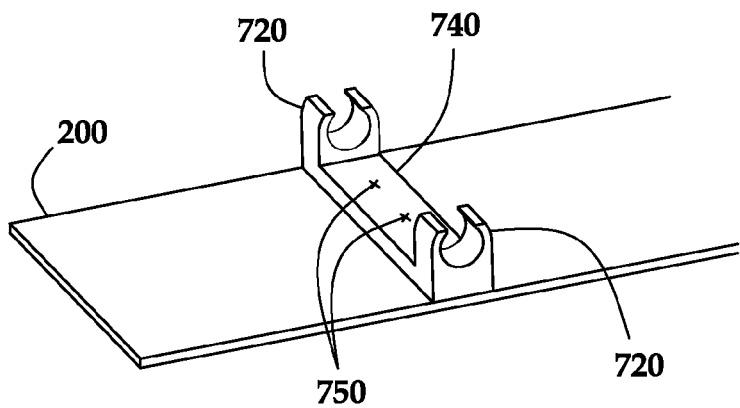
FIG. 7 is a perspective view of a partial electrode assembly having a carrier affixed to the ribbon electrode by welding, according to one illustrative embodiment of the present invention.

In the embodiment shown in FIG. 7, a carrier 740 is disposed substantially orthogonally to the long axis of the ribbon electrode 200 and across substantially the entire short axis of the ribbon electrode 200. The carrier 740 contains a plurality (in the shown embodiment, two) lead attachment structures 720 and is welded to the ribbon electrode 200 at welds 750. The lead attachment structures 720 can be used to physically or electrically couple a lead 235 to the carrier 740 or can increase the surface area of the carrier 740 to enhance adhesion of the insulator 225 to the electrode assembly 125.

Figure 8:
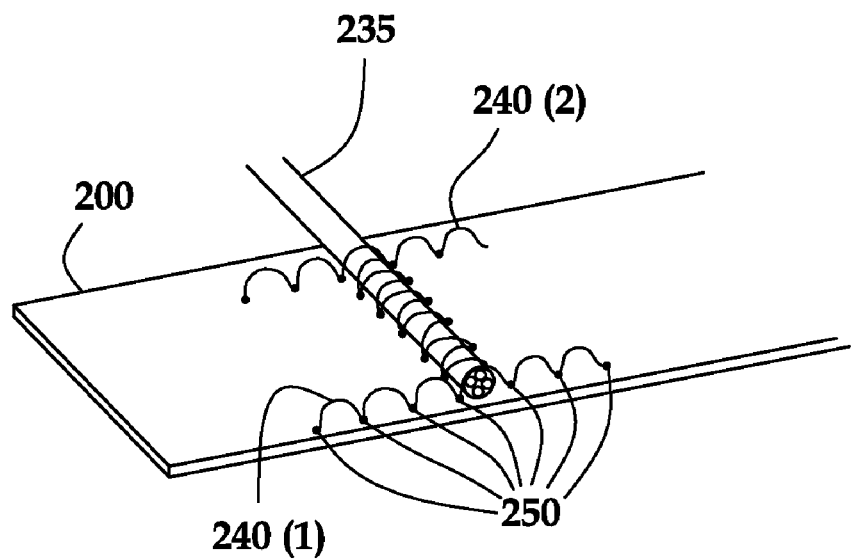
FIG. 8 is a perspective view of a partial electrode assembly having a wire boss affixed to the ribbon electrode by welding and a portion of a lead, according to one illustrative embodiment of the present invention.

FIG. 8 shows a perspective view of an embodiment similar to that of FIG. 3C, wherein two wires 240(1), 240(2) are disposed parallel to the long axis of the ribbon electrode 200 and a lead 235 is physically or electrically coupled thereby to the ribbon electrode 200.

Figure 9:
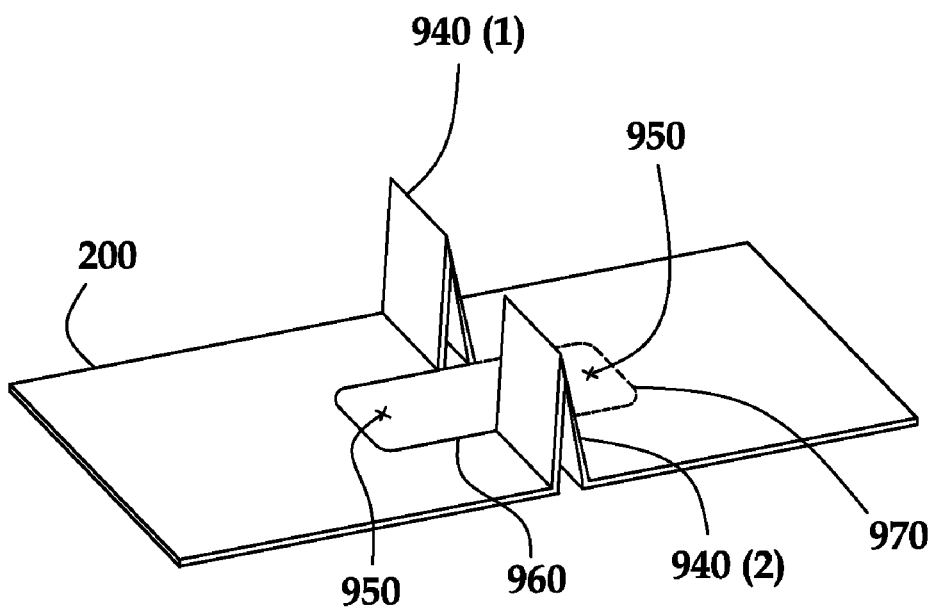
FIG. 9 is a perspective view of a partial electrode assembly having flexible bosses and a cooperating tab-and-slot architecture, according to one illustrative embodiment of the present invention.

FIG. 9 shows a perspective view of an embodiment having flexible bosses 940(1), 940(2) and a cooperating architecture of a tab 960 and a slot 970. In embodiments wherein the ribbon electrode 200 is to be implanted in a cylindrical, spiral, or helical conformation (not shown), the flexible bosses 940(1), 940(2) can flex and the tab 960 can slide within the slot 970 to accommodate the non-flat conformation. At the end of implantation, when the ribbon electrode 200 is in the conformation desired by the skilled artisan, the tab 960 can be fixed in the slot 970 by welds 950.

Figure 10:
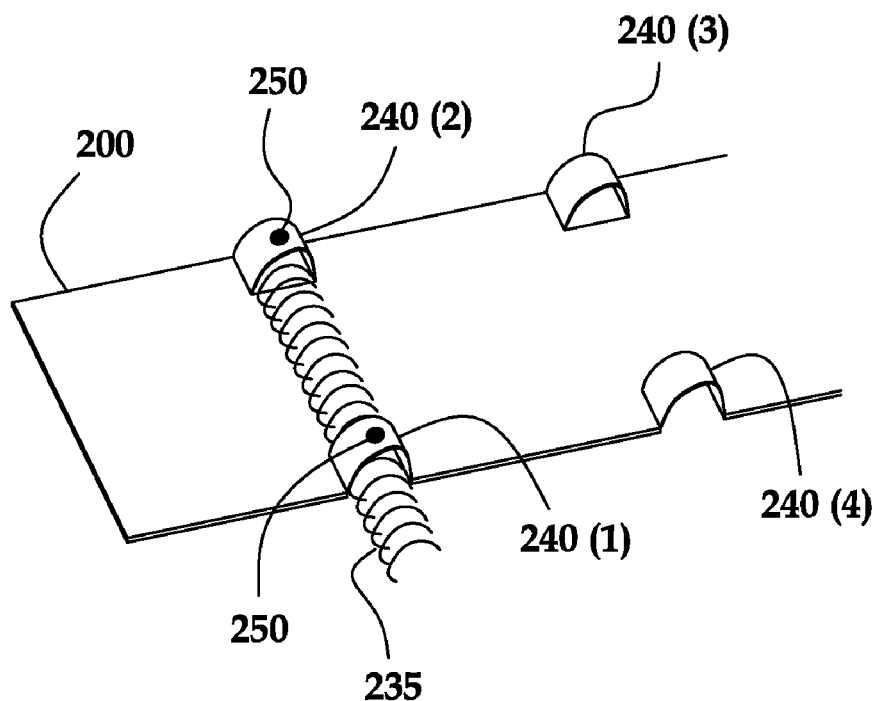
FIG. 10 is a perspective view of a partial electrode assembly having arcuate bosses stamped from the ribbon electrode and a coiled lead, according to one illustrative embodiment of the present invention.

FIG. 10 shows an embodiment similar to that of FIG. 6, insofar as the bosses 240(1), 240(2) are stamped from the ribbon electrode 200. FIG. 10 further shows a lead 235 physically coupled to the bosses 240(1), 240(2) by welds 250.

Figure 11:
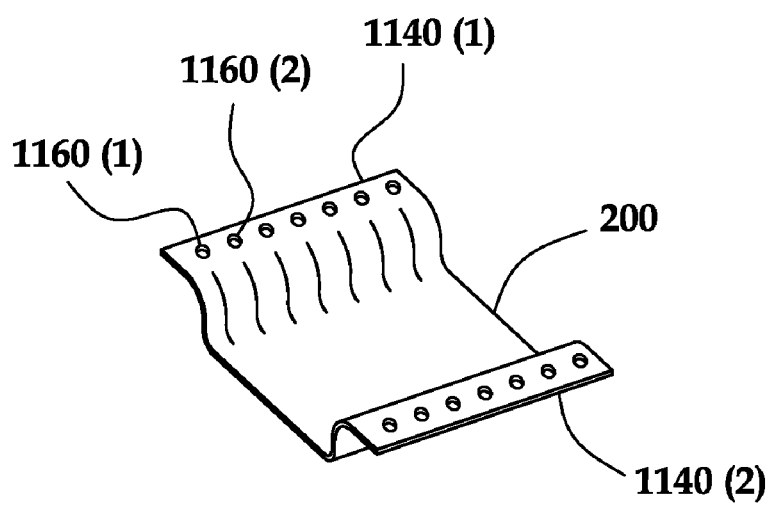
FIG. 11 is a perspective view of a partial electrode assembly having bosses in the form of flanges stamped from the ribbon electrode, according to one illustrative embodiment of the present invention.

FIG. 11 shows a perspective view of an embodiment wherein the ribbon electrode 200 comprises stamped flanges 1140(1), 1140(2). The flanges 1140(1), 1140(2) contain a plurality of apertures 1160(1), 1160(2), etc. The apertures 1160(1), 1160(2), etc. provide points for the physical coupling of a lead 235 (not shown) to the ribbon electrode 200 and further increase the surface area of the flanges 1140(1), 1140(2) which can increase the adhesion of the insulator 225 (not shown) to the ribbon electrode 200.

Figure 4:
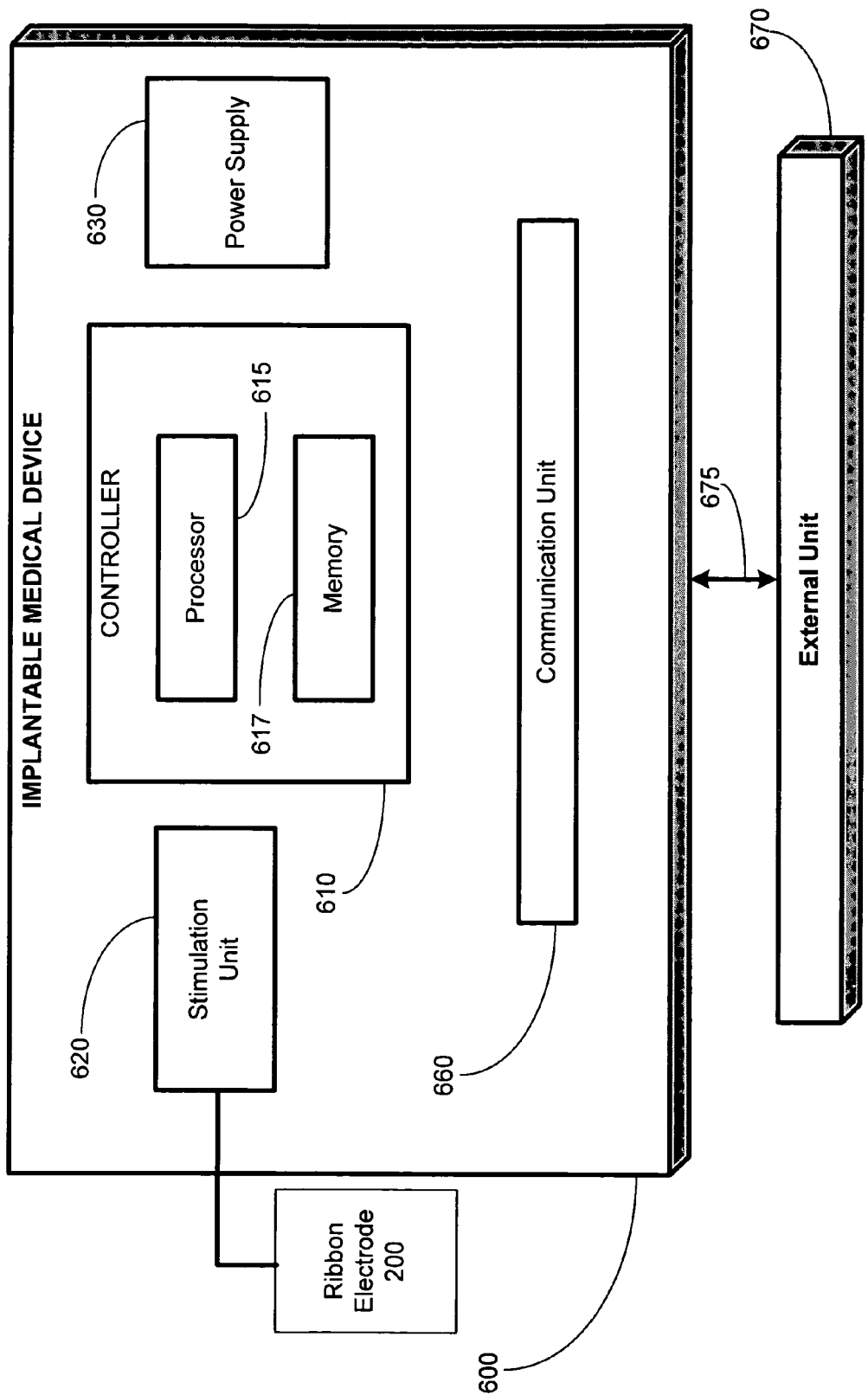
FIG. 4 is a block diagram of an implantable medical device that includes an electrode assembly and an external user interface to communicate with the implantable medical device in accordance with one illustrative embodiment of the present invention.

Turning now to FIG. 4, a block diagram is provided depicting an implantable medical device (IMD) 600 and an external user interface (I/F) 670, in accordance with one illustrative embodiment of the present invention. The IMD 600 may be used to provide electrical stimulation to body tissue, such as nerve tissue, to treat various disorders, such as epilepsy, depression, bulimia, etc. The IMD 600 may be used to treat neuromuscular, neuropsychiatric, cognitive, autonomic, sensory disorders, and other medical conditions.

The IMD 600 may be coupled to various leads, such as lead assembly 122, shown in FIG. 1. Electrical signals from the IMD 600 may be transmitted via the leads 122 to stimulation electrodes associated with the electrode assembly 125. In addition, where sensors are employed, signals from sensor electrodes may travel by leads, such as leads 122, to the IMD 600.

The IMD 600 may comprise a controller 610 that is capable of controlling various aspects of the operation of the IMD 600. The controller 610 is capable of receiving therapeutic data including internal data from memory 617 or external data (not shown) to define and deliver the therapeutic electrical signal to at least one target portion of the human body. For example, the controller 610 may receive manual instructions from an operator externally, or it may perform stimulation based on internal calculations and protocols programmed into or resident in the IMD 600. The controller 610 is preferably capable of affecting substantially all functions of the IMD 600.

The controller 610 may comprise various components, such as a processor 615, a memory 617, and other structures conventional known to those skilled in the art having benefit of the present disclosure. The processor 615 may comprise one or more microcontrollers, microprocessors, etc., that are capable of performing various executions of software components. The memory 617 may comprise various memory portions where the therapeutic data and a number of types of data (e.g., internal data, external data instructions, software codes, status data, diagnostic data, etc.) may be stored and retrieved. The memory 617 may comprise random access memory (RAM), dynamic random access memory (DRAM), electrically erasable programmable read-only memory (EEPROM), flash memory, etc. In one embodiment, the memory 617 may comprise RAM and Flash memory components.

The IMD 600 may also comprise an electrical signal generator 620. The signal generator 620 is capable of generating and delivering a variety of electrical neurostimulation signals to one or more electrodes via leads. A number of lead assemblies 122 may be coupled to the IMD 600. Therapy may be delivered to the lead(s) by the electrical signal generator 620 based upon instructions from the controller 610. The electrical signal generator 620 may comprise various circuitry, such as stimulation signal generators, and other circuitry that receives instructions relating to the type of stimulation to be performed. The electrical signal generator 620 is capable of delivering a controlled current neurostimulation signal over the leads. In one embodiment, the controlled current neurostimulation signal may refer to a prescribed or pre-determined current to a neural tissue of a patient.

The IMD 600 may also comprise a power supply 630. The power supply 630 may comprise one or more cells, voltage regulators, etc., to provide power for the operation of the IMD 600, including delivering stimulation. The power supply 630 may comprise a power supply source that in some embodiments is rechargeable. The power supply 630 provides power for the operation of the IMD 600, including electronic operations and the stimulation function. The power supply 630, in one embodiment, may comprise a lithium/thionyl chloride cell or, more preferably, a lithium/carbon monofluoride (LiCFx) cell. It will be apparent to persons of skill in the art that other types of power supplies, e.g., high charge-density capacitors, may also be used instead of (or in addition to) the power supply 630.

The IMD 600 also comprises a communication interface (I/F) 660 capable of facilitating communications between the IMD 600 and various devices. The communication interface 660 is capable of providing transmission and reception of electronic signals to and from the external user interface 670. The external user interface 670 may be a handheld device, preferably a handheld computer or PDA, but may alternatively comprise any other device that is capable of electronic communications and programming.

The external user interface 670 may comprise a programming device that is capable of programming various modules and stimulation parameters of the IMD 600. In one embodiment, the programming device is capable of executing a data-acquisition program. The programming device may be controlled by a medical professional, such as a physician, at a base station in, for example, a doctor's office. The programming device may download various parameters and program software into the IMD 600 for programming and controlling its operation. The programming device may also receive and upload various status conditions and other data from the IMD 600.

The communication user interface 660 may comprise hardware, software, firmware, or any combination thereof. Communications between the external user interface 670 and the communication user interface 660 in the IMD 600 may occur via a non-invasive, wireless or other type of communication, illustrated generally by line 675 in FIG. 6. Various software or firmware applications may be loaded into the programming device for programming the external user interface 670 for communications with the IMD 600. In one embodiment, the external user interface 670 may be controlled by Windows® CE operating system offered by Microsoft Corporation of Redmond, Wash.

The IMD 600 may deliver an electrical neurostimulation signal to the nerve 127 or a nerve fascicle within a nerve trunk. In one embodiment of the present invention, methods, apparatus, and systems provide the neurostimulation signal to a cranial nerve, which is preferably a vagus nerve. By using the neurostimulation signal to treat a medical condition, the IMD 600 may provide a neurostimulation therapy to a patient, according to one embodiment of the present invention. In one embodiment, such stimulating or modulating signals are applied to the nerve 127 via the ribbon electrode 200, and intrinsic nerve signals may be detected by the ribbon electrode 200 for processing in sense circuitry, by a signal generator.

Consistent with one embodiment, the IMD 600 may be a neurostimulator device capable of treating a disease, disorder or condition by providing electrical neurostimulation therapy to a patient. To this end, the IMD 600 may be implanted in the patient at a suitable location to treat a depression disorder, an epilepsy disorder, a gastric-related disorder, a hormonal disorder, a reproductive disorder, a metabolic disorder, a hearing disorder, a pain disorder, or a heart rhythm disorder.

To this end, the IMD 600 may provide stimulation for at least one of the trigeminal, glossopharyngeal, and vagus nerves, or other parasympathetic or sympathetic nerves, and may improve the condition of patients suffering from different neurological or neurologically related diseases or disorders.

IMDs 600 that may be used in the present invention include any of a variety of electrical stimulation devices, such as a neurostimulator capable of stimulating a neural structure in a patient, especially for stimulating a patient's cranial nerve such as a vagus nerve. Although the IMD 600 is described in terms of cranial nerve stimulation, and particularly vagus nerve stimulation (VNS), a person of ordinary skill in the art would recognize that the present invention is not so limited. For example, the IMD 600 may be applied to the stimulation of other cranial nerves, such as the trigeminal or glossopharyngeal nerves, or other neural tissue, such as one or more brain structures of the patient, spinal nerves, and other spinal structures. In one alternative embodiment, the invention may be implemented in a spinal cord stimulator (SCS).

The IMD 600 may be a single device or a pair of devices, is implanted and electrically coupled to the lead(s) 235, which are in turn coupled to the electrode(s) 200 coupled to the left or right branches of the vagus nerve, for example. In one embodiment, the ribbon electrode 200 may include a set of stimulating electrode(s) separate from a set of sensing electrode(s). In another embodiment, the same electrode(s) may be deployed to stimulate and to sense. A particular type or a combination of electrodes may be selected as desired for a given application. For example, an electrode suitable for coupling to a vagus nerve may be used. The ribbon electrodes 200 preferably comprise at least a bipolar stimulating electrode pair, although unipolar electrodes may be used in some embodiments.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An electrode assembly, comprising:
   a ribbon electrode formed in a shape selected from the group consisting of substantially cylindrical, substantially spiral, and substantially helical conformation having a first surface and a second surface;
   a plurality of formations disposed on the second surface of the ribbon electrode, wherein each formation has a third surface substantially not in contact with the second surface of the ribbon electrode thereby forming a channel, and at least one formation is electrically conducting;
   a lead wire electrically coupled to the at least one electrically conducting formation through that formations' channel; and
   an insulating material contacting substantially the entire second surface of the ribbon electrode and substantially the entire third surface of each formation;
   wherein the insulating material is substantially not in contact with the first surface of the ribbon electrode; and
   wherein the electrode assembly is implantable.

2. An electrode assembly, comprising:
   a ribbon electrode having a first surface and a second surface;
   a plurality of bosses disposed on the second surface of the ribbon electrode, wherein each boss has a third surface substantially not in contact with the second surface of the ribbon electrode thereby forming a channel, and at least one boss is electrically conducting;
   a lead wire electrically coupled to the least one electrically conducting boss through that boss's channel; and
   an insulator contacting substantially the entire second surface of the ribbon electrode and substantially the entire third surface of each boss;
   wherein the insulator is substantially not in contact with the first surface of the ribbon electrode; and
   wherein the electrode assembly is implantable.

3. The electrode assembly of claim 2, wherein at least one boss is integrally formed with the ribbon electrode.

4. The electrode assembly of claim 3, wherein at least one boss is stamped or crimped from the ribbon electrode.

5. The electrode assembly of claim 2, wherein at least one boss is separately formed from the ribbon electrode and is subsequently affixed to the second surface of the ribbon electrode.

6. The electrode assembly of claim 5, wherein the at least one boss is welded or crimped to the ribbon electrode.

7. The electrode assembly of claim 2, wherein a boss is selected from the group consisting of a saddle, a tunnel, and a wire.

8. The electrode assembly of claim 2, wherein the insulator is a silicone polymer.

9. The electrode assembly of claim 2, wherein the ribbon electrode has a flat, cylindrical, spiral, or helical conformation.

10. An implantable medical device system comprising:
    an implantable medical device for generating an electrical signal;
    an electrode assembly, comprising:
    a ribbon electrode having a first surface and a second surface;
    a plurality of bosses disposed on the second surface of the ribbon electrode, wherein each boss has a third surface substantially not in contact with the second surface of the ribbon electrode thereby forming a channel comprising an arcuate central portion, and at least one boss is electrically conducting; and
    an insulator contacting substantially the entire second surface of the ribbon electrode and substantially the entire third surface of each boss;
    wherein the insulator is substantially not in contact with the first surface of the ribbon electrode; and
    a lead wire electrically coupled to both the implantable medical device and at least one electrically conducting boss through that boss's channel.

11. The implantable medical device system of claim 10, wherein at least one boss is integrally formed with the ribbon electrode.

12. The implantable medical device system of claim 11, wherein at least one boss is stamped or crimped from the ribbon electrode.

13. The implantable medical device system of claim 10, wherein at least one boss is separately formed from the ribbon electrode and is affixed to the second surface of the ribbon electrode.

14. The implantable medical device system of claim 13, wherein at least one boss is welded or crimped to the ribbon electrode.

15. The implantable medical device system of claim 10, wherein at least one boss is selected from the group consisting of a saddle, a tunnel, and a wire.

16. The implantable medical device system of claim 10, wherein the insulator is a silicone polymer.

17. The implantable medical device system of claim 10, wherein the ribbon electrode has a flat, cylindrical, spiral, or helical conformation.

* * * * *